United States Patent [19]

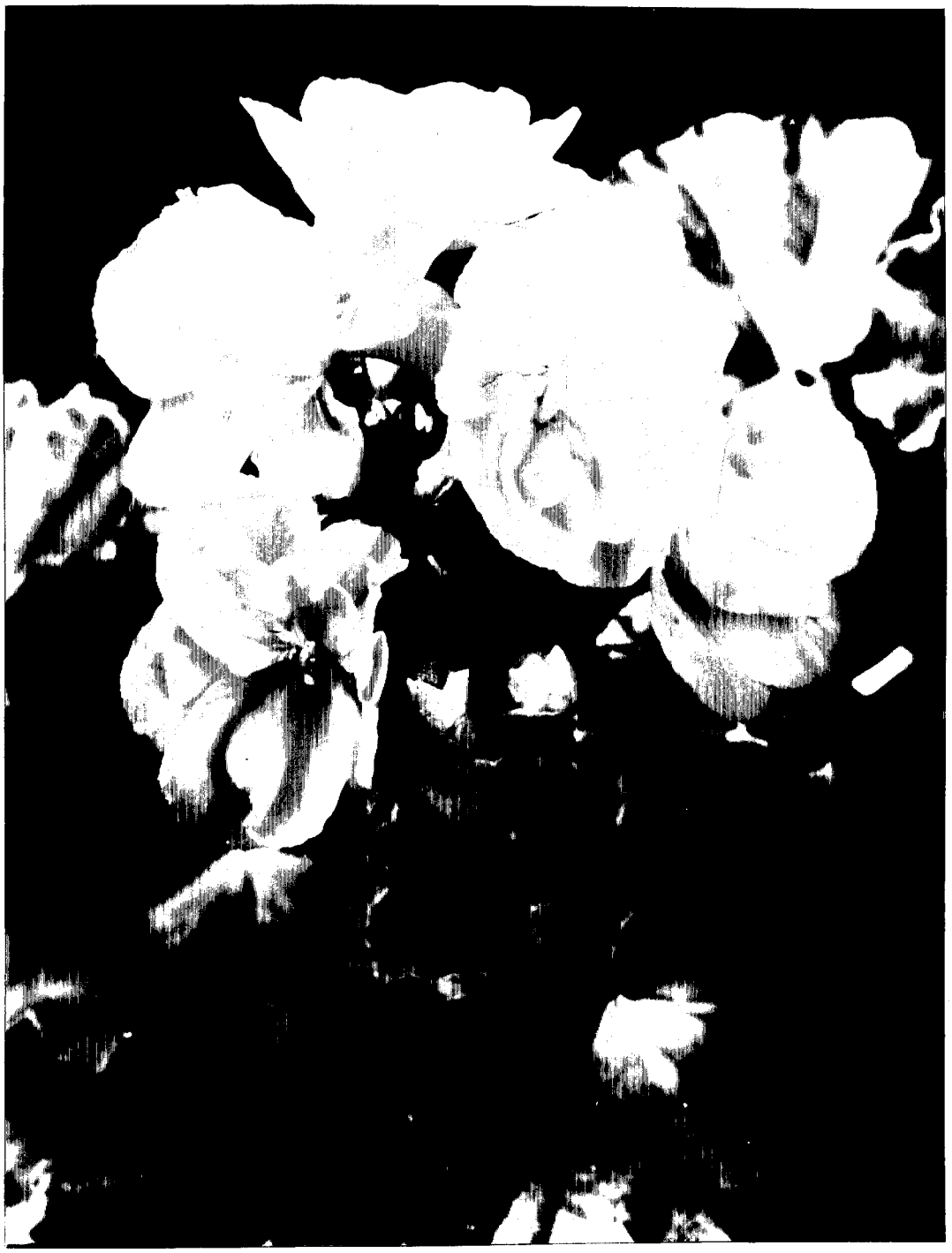

Buck

[11] Patent Number: Plant 5,757

[45] Date of Patent: Jul. 1, 1986

[54] GERANIUM PLANT NAMED ORANGEADE

[75] Inventor: Griffith J. Buck, Ames, Iowa

[73] Assignee: Iowa State University Research Foundation, Inc., Ames, Iowa

[21] Appl. No.: 641,266

[22] Filed: Aug. 16, 1984

[58] Field of Search ..... Plt./68

[51] Int. Cl.[4] ..... A01H 5/00

[52] U.S. Cl. ..... Plt./68

*Primary Examiner*—James R. Feyrer

*Attorney, Agent, or Firm*—Tilton, Fallon, Lungmus

[57] ABSTRACT

A new variety of geranium plant distinguished by the scarlet color (Mandarin Red) of its flowers, its vigorous and floriferous growth under the high summer temperatures and humidities commonly found in Midwestern United States, and its strong field tolerance to foliar diseases such as *Botrytis cinerea* (gray mold).

1 Drawing Figure

BACKGROUND OF THE NEW PLANT

This new geraniumn cultivar originated as a seedling produced by my crossing "Hazel" (U.S. Plant Pat. No. 4,040) as the seed parent with an unnamed variety in my stock resulting from ("Regina"×"Highfields' Pride") (both unpatented) crossed with "Pearlie Mae Red" (U.S. Plant Pat. No. 4,039) as the pollen parent. The new cultivar was discovered by me at Iowa State University Horticulture Greenhouses, Ames, Iowa, in 1978 and resulted from breeding efforts commenced by me in about 1956 at that University. This new plant was selected for propagation because of the distinctive scarlet color of its flowers, its ability to flower profusely and grow vigorously under high temperature and humidity conditions, and its resistance to foliar diseases, particularly *Botrytis cinerea.* Propagation under my direction at Iowa State University, Ames, Iowa, has been carried out by means of cuttings and has been continued through successive generations to demonstrate that the distinctive characteristics of the plant are reproducable from generation to generation.

DESCRIPTION OF THE DRAWING

This new geranium plant is illustrated by the accompanying photographic drawing which shows blooms, buds, and foliage of the plant in full color, such colors of the drawing being as true to those of the plant as can be reasonably obtained with conventional professional photographic procedures.

DESCRIPTION OF THE NEW PLANT

The following is a description in detail of my new geranium plant variety with color designations according to The Royal Horticultural Society Colour Chart (R.H.S.C.C.).

THE PLANT

Origin: Seedling.

Parentage:

*Seed parent.*—"Hazel" (U.S. Plant Pat. No. 4,040).

*Pollen parent.*—An unnamed variety by crossing "Pearlie Mae" (U.S. Plant Pat. No. 4,039) with an unnamed variety resulting from "Regina" crossed with "Highfields' Pride" (both unpatented).

Classification:

*Botanic.*—Pelargonium hortorum.

*Commercial.*—Garden geranium.

Form: Bush.

Height: 35 to 45 cm.

Growth: Vigorous, erect, and bushy.

Strength: Sturdy; does not break apart readily in wind and rain.

Foliage: Abundant quantity.

*Leaves.*—Size: About 10 to 13 cm. in diameter. Shape: Round-cordate, with several rounded lobes and serrate margins. Texture: Leathery, softly firm to the touch, and slightly pubescent on both surfaces. Color: Upper side: Yellow-Green 146A (R.H.S.C.C.)with indistinct center zone of lighter Yellow-Green 146C (R.H.S.C.C.).Under side: Olive Green 146B (R.H.S.C.C.). Ribs and Veins — Not prominent on upper surface but conspicuous on under side of leaf.

Petioles: 9.5 to 10.5 cm long.

THE BUD

Size:

*Large.*—1.2 to 2.1 cm. long by 0.8 to 1.2 cm. in diameter.

Shape: Pointed ovoid.

Opening: Bud opens slowly.

Color:

*When sepals first divide and later when they begin to unfurl.*—Poppy Red 40D (R.H.S.C.C.) over a white base.

Sepals: Separated sepals which stand up and which curl back as flower opens. Their inside color is Yellow-Green, 146C(R.H.S.C.C.); outside color is Yellow-Green 146B (R.H.S.C.C.) with occasional light red tinge on side exposed to sun.

THE FLOWER

Blooming habit: Continuous and profuse throughout summer; under glass and with adequate photoperiod and temperature, it will bloom continuously throughout the year.

Size: Very large. Diameter is 11 to 15 cm., depth is 5.5 to 8 cm.

Borne: Inflorescence is an umbel and is borne singly.

Shape: Compact; somewhat globular.

Florets:

*Form.*—Cup-shaped when bloom first opens; later flattens to form a shallow cup.

*Petals.*—6 to 8 in number; arrangement is imbricate; shape is obovate.

*Color.*—Both the outer and inner petals are Mandarin Red 40B (R.H.S.C.C.) with lighter bases of Poppy Red 40D (R.H.S.C.C.), the outer petals also having white claws at their bases; on their reverse sides, the petals are Mandarin Red 40C (R.H.S.C.C.) over white bases. The petals are satiny in appearance.

Petaloids: 1 to 4 in number. Their size is 1.5 to 2 cm. long and 1 to 1.5 cm. wide, and their color is Mandarin Red 40B (R.H.S.C.C.) with their reverse sides Poppy Red 40D (R.H.S.C.C.).

Pedicel: 2.5 to 3 cm. long. The pedicel is strong and Yellow-Green 146C (R.H.S.C.C.), tinted reddish on parts exposed to the sun.

Peduncle: Sturdy and upright with a length of 8 to 11 cm. and Yellow-Green color 146C (R.H.S.C.C.) tinted red on sides exposed to the sun.

Persistence: Flowers hang on and dry.

Lasting quality: Approximately 7 days, both on the plant and as a cut flower.

Disease resistance: The plant has good tolerance to *Botrytis cinerea.*

REPRODUCTIVE ORGANS

Stamens:

*Anthers.*—7 to 10 in number with a length of about 0.3 cm. in a cylindrical arrangement.

*Filaments.*—Length of 0.4 to 0.7 cm. and of a white color.

Pollen.—Brownish yellow in color.

Pistils: Single with a length of 0.7 to 0.9 cm. and a color of Red 40D (R.H.S.C.C.).

Ovaries: 5-celled.

Fruit: Partially fertile. The shape is ovoid with a long "beak" and a brownish-black color at maturity.

This variety of geranium plant has a floral color similar to, but more orange than, the color of "Orange Glow" (unpatented). The plant habit is similar to that of its principal parents "Hazel" (U.S. Plant Pat. No. 4,040) and "Pearlie Mae Red" (U.S. Plant Pat. No. 4,039) in that it is also tolerant of high temperatures and humidity and has the ability to flower profusely and grow vigorously under those climatic conditions. This new cultivar has shown high tolerance under field conditions to gray mold (*Botrytis cinerea*) and retains the desirable traits of its two principal parents of a profuse flowering habit resulting from a relatively short time period for the initiation of inflorescences which are produced on a 2 to 4 node cycle.

I claim:

1. A new and distinct geranium cultivar substantially as herein shown and described, characterized by its abundant production of large umbel-form clusters of very large florets, the red-orange coloring of its flowers, and its resistance to foliar diseases, particularly *Botrytis cinerea.*

* * * * *